US005735287A

United States Patent [19]
Thomson

[11] Patent Number: 5,735,287
[45] Date of Patent: *Apr. 7, 1998

[54] BIODEGRADABLE AIR TUBE AND SPIROMETER EMPLOYING SAME

[75] Inventor: Ronald A. Thomson, San Clemente, Calif.

[73] Assignee: Desert Moon Development Limited Partnership, Dana Point, Calif.

[*] Notice: The term of this patent shall not extend beyond the expiration date of Pat. No. 5,564,432.

[21] Appl. No.: 654,303

[22] Filed: May 28, 1996

Related U.S. Application Data

[62] Division of Ser. No. 274,470, Jul. 13, 1994, Pat. No. 5,564,432.

[51] Int. Cl.$^6$ ........................................... A61B 5/087
[52] U.S. Cl. ........................................ 128/725; 73/861.52
[58] Field of Search .................................. 128/716, 725, 128/726; 73/861.52; 482/13

[56] References Cited

U.S. PATENT DOCUMENTS

| D. 272,184 | 1/1984 | Karpowicz . |
|---|---|---|
| 4,122,842 | 10/1978 | Pikul . |
| 4,403,514 | 9/1983 | Osborn . |
| 4,640,293 | 2/1987 | Garbe . |
| 4,807,641 | 2/1989 | Boehringer et al. . |
| 4,905,709 | 3/1990 | Bieganski et al. . |
| 4,989,456 | 2/1991 | Stupecky . |
| 4,995,400 | 2/1991 | Boehringer et al. . |
| 5,038,621 | 8/1991 | Stupecky . |
| 5,038,773 | 8/1991 | Norlien et al. . |
| 5,060,655 | 10/1991 | Rudolph . |
| 5,111,827 | 5/1992 | Rontala . |
| 5,137,026 | 8/1992 | Waterson et al. . |
| 5,277,195 | 1/1994 | Williams . |
| 5,277,196 | 1/1994 | Hankinson et al. . |
| 5,287,851 | 2/1994 | Beran et al. . |
| 5,288,318 | 2/1994 | Mayer et al. . |
| 5,292,782 | 3/1994 | Bastioli et al. . |
| 5,296,526 | 3/1994 | Delrue et al. . |
| 5,305,762 | 4/1994 | Acorn et al. . |
| 5,379,650 | 1/1995 | Koford et al. . |
| 5,564,432 | 10/1996 | Thomson ............................ 128/725 |

OTHER PUBLICATIONS

Dawson, Pulmonary Function Testing Guidelines and Controversies, Chapter 9 pp. 91–97, 1982.
Manual of Pulmonary Function Testing, pp. 154–158.
Halliday et al, Fundamentals of Physics, Second Edition, pp. 277–284.
MultiSPIRO–SX Specifications (Date unknown).
Respiradyne®, Pulmonary Function/Ventilation Monitor Operation Manual (1990).

Primary Examiner—Lee S. Cohen
Attorney, Agent, or Firm—Frank J. Uxa

[57] ABSTRACT

Disclosed is an air tube for use in a spirometer. This air tube is disposable and is at least partially, preferably completely, biodegradable, so that is can be economically produced and discarded after use by a single spirometer user. Cross-patient contamination and expensive sterilization procedures are thus avoided. In addition, making this air tube biodegradable allows for the use of plentiful and inexpensive materials of construction, such as cardboard, paper, biodegradable polymers and the like, and reduces the environmental burden caused by disposing of this component.

19 Claims, 3 Drawing Sheets

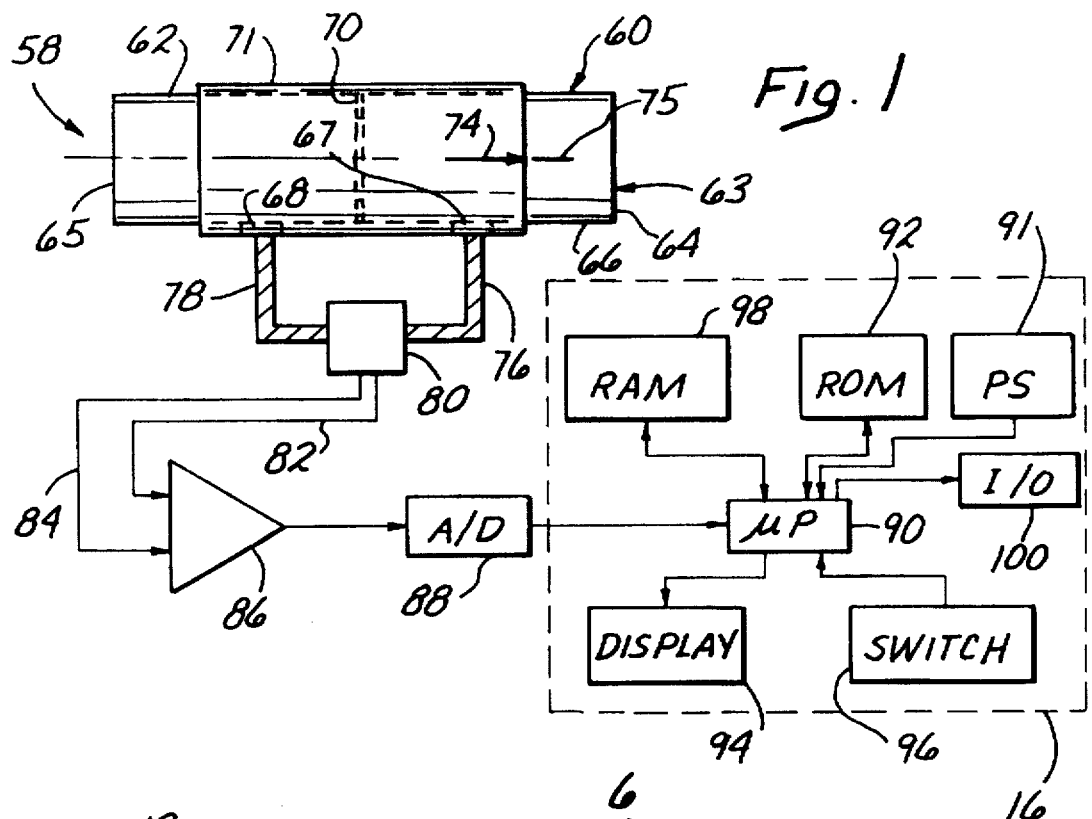
Fig. 1
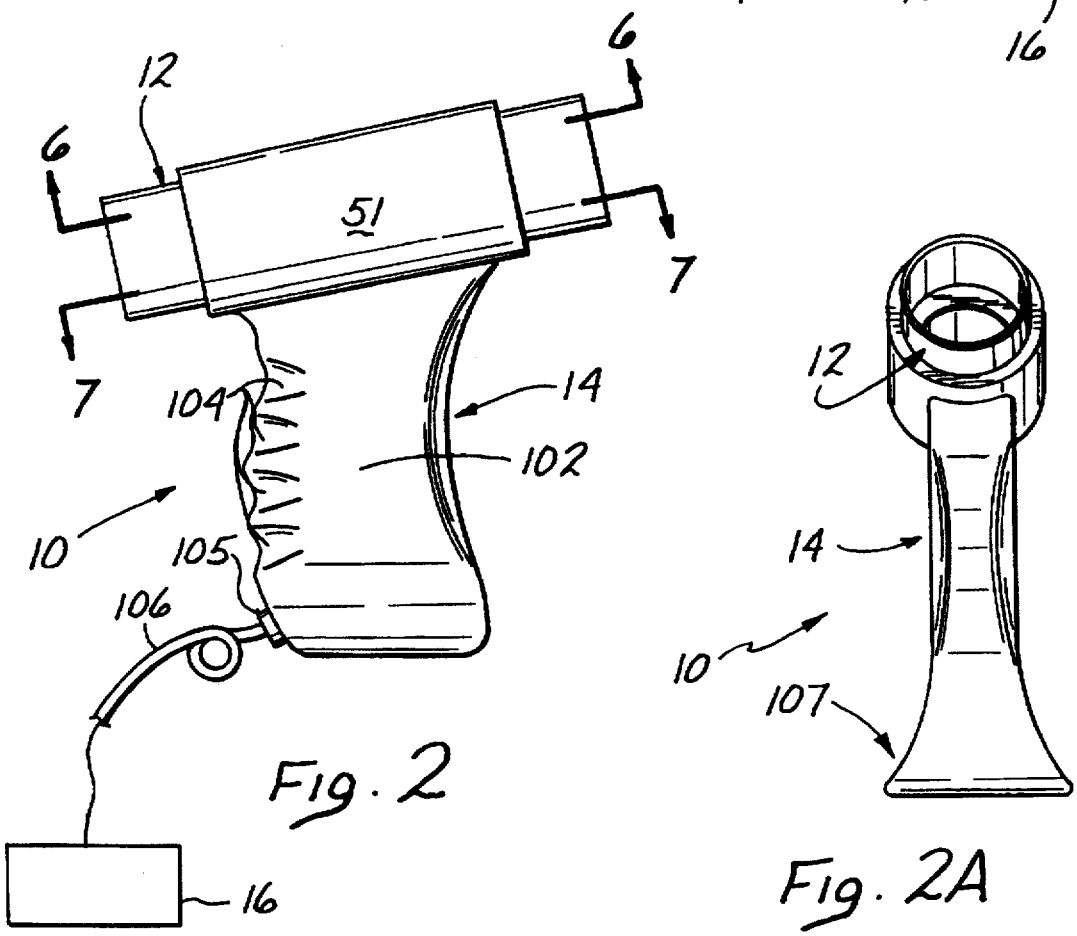
Fig. 2
Fig. 2A

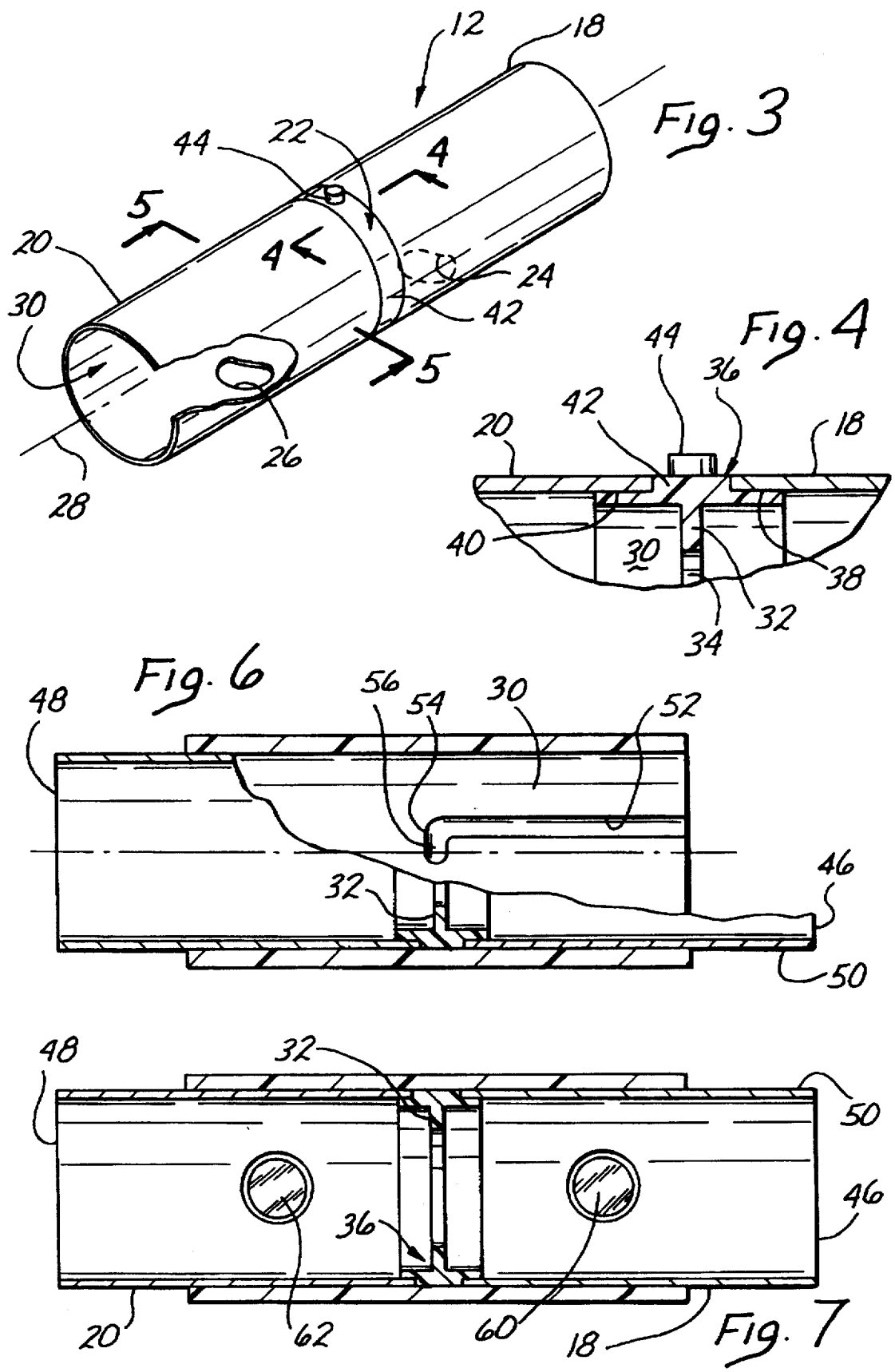

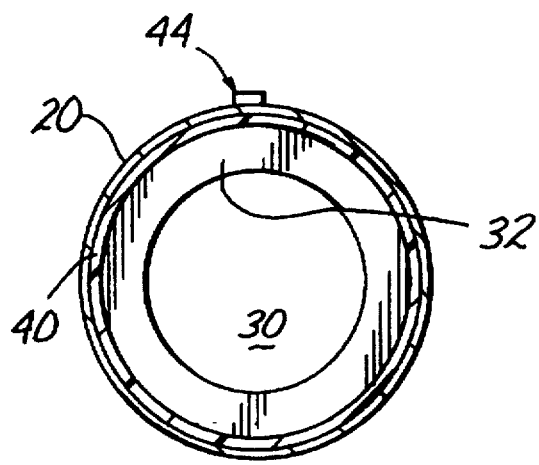
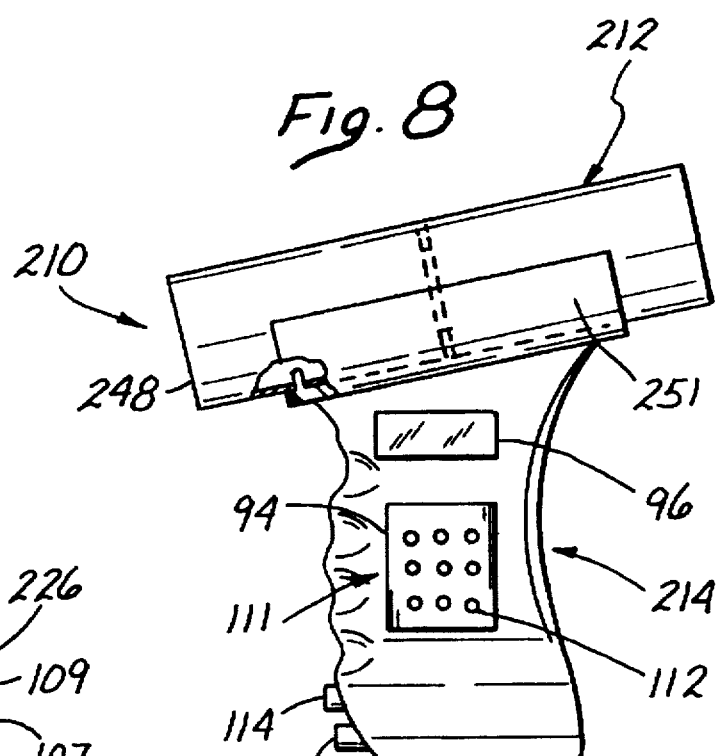
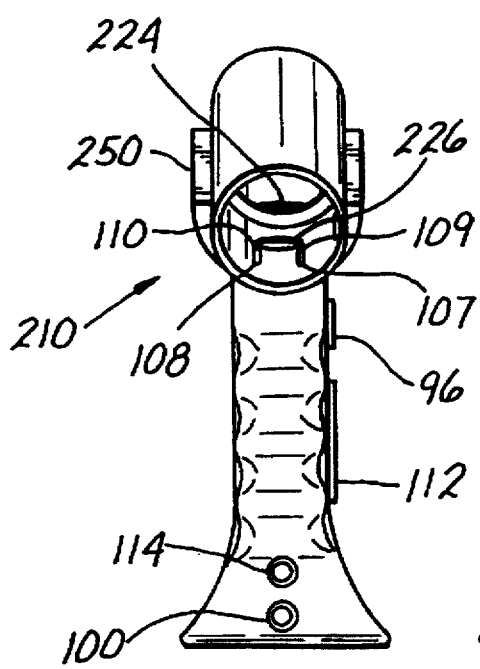

BIODEGRADABLE AIR TUBE AND SPIROMETER EMPLOYING SAME

This is a division of application Ser. No. 08/274,470, filed Jul. 13, 1994, now U.S. Pat. No. 5,564,432.

BACKGROUND OF THE INVENTION

The present invention relates to air tubes for use with spirometers, and to spirometers using such air tubes. More particularly, the present invention relates to air tubes which are disposable and at least partially biodegradable, and to spirometers, preferably differential pressure spirometers, which employ such air tubes.

Spirometers are devices used to measure the volume and flow rate of gas exhaled by a user or patient, for example, a human being. These measurements are important for physiological studies and for diagnostic analysis of the pulmonary performance of the spirometer user. For example, the effects of various medicines used to treat patients with pulmonary or asthmatic problems can be analyzed by monitoring the volume and flow rate of gas exhaled before and after the administration of medication. Several devices are available on the market which are known as pneumotachs, such as the Fleisch Pneumotach. These devices depend on a laminar air flow past a resistance element. Other spirometers employ more sophisticated electronics so that laminar flow is not needed.

Measuring the pressure difference or differential pressure of exhaled gas across an element which creates or causes the pressure difference is the basis for differential pressure spirometers. In such differential pressure spirometers, it is important that the air tube (pneumotach) be precisely configured and positioned, for example, relative to the pressure sensing and electronics systems of the spirometers so that measurements can be reliably and reproducably made. Such precisely configured pneumotachs, rather than being disposable, are made out of metals or durable plastics to be long lasting and effective after many uses without structural degradation. See, for example, Waterson et al U.S. Pat. No. 5,137,026, the disclosure of which is hereby incorporated in its entirety by reference herein.

Since most spirometers involve passing exhaled gas directly from the respiratory system of a user into the instrument for measuring, one important complication of using such devices is contamination from one patient to another patient if the same spirometer is employed by both.

Various approaches to overcoming this contamination problem have been suggested. A particularly popular approach is to use a disposable mouthpiece and filter over the inlet to the spirometer. The patient using the spirometer comes in contact only with the mouthpiece and is able, at least in theory, to avoid contaminating the remainder of the device. Drawbacks to this approach include the relative expense of such mouthpieces/filters, and the relative inefficiency of such systems.

Another approach to overcoming this contamination problem is to sterilize the portion or portions of the spirometer which come in contact with the user and/or exhaled air. Drawbacks to this approach include having to spend additional capital on sterilization equipment, having to monitor the operation and efficacy of the sterilization equipment, and having to purchase relatively durable and expensive spirometers to withstand the sterilization procedures.

A third alternative that has been suggested is the use of disposable spirometer components. See, for example, Norlien et al U.S. Pat. No. 5,038,773; Acorn et al U.S. Pat. No. 5,305,762; Karpowicz U.S. Pat. Des. 272,184; Boehringer et al U.S. Pat. No. 4,807,641; and Bieganski et al U.S. Pat. No. 4,905,709. Such previous disposable spirometer components have been made out of durable plastics or medical grade metals so that, even though they are disposable, the cost of producing such components is relatively high. In addition, such disposable components are relatively difficult to dispose of, for example, because they are made of durable and long lasting materials.

It would be advantageous to provide spirometers and spirometer components which avoid cross-patient contamination and which can be economically, conveniently and effectively produced and used.

SUMMARY OF THE INVENTION

New air tubes for use in spirometers and spirometers including such air tubes have been discovered. The present air tubes are disposable so that after one patient uses the air tube it is removed from the spirometer and is disposed of. Importantly, the air tube is at least partially, preferably completely, biodegradable.

As used herein, the term "biodegradable" means that the component or material is decomposable into more environmentally acceptable components, such as carbon dioxide, water, methane and the like, by natural biological processes, such as microbial action, for example, if exposed to typical landfill conditions, in no more than five years, preferably no more than three years, and still more preferably no more than one year.

Having the air tube biodegradable provides substantial advantages. First, when the air tube is disposed of, the burden on the environment of such disposal is reduced relative to, for example, a non-biodegradable air tube, such as those made out of conventional plastics or metals. In addition, because the air tube is biodegradable, it can be made of materials which are inexpensive and plentiful (readily available). Thus, the present air tubes are relatively inexpensive, easy and straightforward to produce, requiring little or no sophisticated production equipment. Since the present air tubes can be made economically, replacing a used air tube with a new air tube is done without substantial economic impact. In addition, the present air tubes can be replaced in the spirometer very easily. These advantages promote operator compliance in that the spirometer operator (for example, the care provider or the patient operating the spirometer) is more likely to change the present air tubes after each patient or treatment, thus reducing the risks of contamination and the spread of diseases, for example, tuberculosis and other respiratory system disorders, AIDS, other systemic conditions and the like.

Spirometers employing the present air tubes provide cost effective, reliable and reproducible (from air tube to air tube) measurements of the pulmonary performance of the user, with reduced risk of contamination. In short, the present disposable, biodegradable spirometer air tubes are inexpensive and easy to produce to acceptably precise specifications (for reproducible performance), are effective and reliable in use, and are conveniently and effectively disposed of in an environmentally acceptable or safe manner to reduce the risks of contamination caused by spirometer use.

In one broad aspect, the present invention is directed to air tubes for use in spirometers. The present air tubes comprise a tubular portion which defines an open inlet, an open, preferably opposing, outlet and a hollow space therebetween. The tubular portion is sized and adapted to be removably coupled to the housing of a spirometer. The air tube is disposable, i.e., can be removed or decoupled from the spirometer housing and disposed of without disposing of the housing. At least a portion, preferably at least major portion, that is at least about 50% by weight, and more preferably substantially all, of the tubular portion is biodegradable. Preferably, the open inlet is sized and adapted to be received in the mouth of the user of the spirometer. Thus, this open inlet and the area of the tubular portion near the open inlet act as a mouthpiece for the spirometer so that the user or patient using the spirometer can exhale into the air tube directly through the open inlet. No separate and/or specially configured (relative expensive) mouthpiece/filter is needed when using the present air tubes.

In addition, the present air tubes include a resistive element which is located in the hollow space of the tubular portion. This resistive element is sized and adapted to cause a pressure difference or differential as air flows in the hollow space across this element. Preferably at least a portion, more preferably at least major portion, and still more preferably substantially all, of the resistive element is biodegradable.

Two through ports are provided in the tubular portion. Each of these through ports opens directly into the hollow space defined by the tubular portion and is spaced apart, preferably equidistantly spaced apart, from the resistive element. These through ports provide communication between the hollow space of the tubular portion and the pressure sensing assembly of the spirometer.

The tubular portions, and preferably the resistive elements, of the present air tubes are at least partially made of biodegradable materials. Preferred biodegradable materials of construction include cardboard, paper, biodegradable polymeric materials and the like and mixtures thereof. In one particularly useful embodiment, the tubular portion is made of cardboard or paper or mixtures thereof, more preferably produced by methods analogous to those conventionally used to produce tubes around which are wound bathroom tissue. Such production methods often include forming a cardboard or paper tube over a mandrel or a like implement and then cutting the resulting tube to the desired length. In the event that the tubular portion is made from a biodegradable polymeric material such tubes can be formed by conventional polymer molding techniques.

The use of tubular portions made out of cardboard, paper and the like is particularly advantageous because such components are relatively easy and inexpensive to make and, in addition, promote operator compliance in disposing of the air tube after each use. This is so because such a tubular portion, particularly in the area around the open inlet (which is preferably used as a mouthpiece) retains moisture (from the saliva of the patient) and becomes and remains wet. This wet appearance automatically warns the next spirometer user that the air tube has been used previously. Thus, this next user is more likely to demand that the air tube be replaced, thereby reducing the risks of cross-patient contamination.

The present resistive elements can have any suitable shape or configuration, for example, of a screen, a partial restriction in the hollow space of the tubular portion or other convenient configuration, to provide an acceptably measurable pressure differential as air flows across the resistive element. This pressure differential, for a given rate of flow of air, should be essentially the same from air tube to air tube so that no recalibration of the precalibrated spirometer is required after replacing the air tube. Therefore, it is preferred that the resistive elements have substantially the same precise structure, resistive element to resistive element. In one particularly useful embodiment, the resistive element is made of a biodegradable polymeric material. This feature facilitates producing the resistive elements to a precise, reproducible configuration.

In addition, the resistive elements should be placed relative to the tubular portion so that the pressure difference for any given rate of flow of air across the resistive element is the same from air tube to air tube. The resistive element is preferably located transverse to the longitudinal axis of the tubular portion.

The resistive element can be placed in the tubular portion in any suitable manner, for example, by press fitting the resistive element into the hollow space, by adhering (for example, using biodegradable adhesives) the resistive element to the interior wall of the tubular portion or by joining two separate segments of the tubular portion together with the resistive element therebetween. Other methods or techniques for placing the resistive elements in the tubular portions may be employed. Preferably, the resistive elements of the present air tubes designed for use in the same spirometer are structured and configured essentially the same, so that no recalibration of or other adjustment to the spirometer is needed because one air tube is replaced by another air tube.

In a preferred embodiment, the present air tubes further comprise a positioning means or sub-system adapted to cooperate with the housing of the spirometer to properly position the air tube relative to the housing of the spirometer for use. Any suitable positioning means may be employed to properly orient the air tube relative to the housing of the spirometer, for example, so that the through ports of the air tube are properly aligned and communicate with the pressure sensing assembly of the spirometer.

In one specific embodiment, the positioning means includes a projection sized and adapted to cooperate with a notch in the housing of the spirometer.

In another specific embodiment, the positioning means includes at least one, preferably two, positioning ports in the tubular portion sized and adapted to cooperate with at least one, preferably two, positioning projections in the housing of the spirometer. This is a particularly useful embodiment since the positioning port or ports can be easily placed in the tubular portion of the air tube. Also, since the housing of the spirometer is often a molded polymeric component, the positioning projections or projections can be easily formed in the spirometer housing.

An air tube in accordance with the present invention can be snugly fitted into a hollow open space defined by a spirometer housing tube so that the through ports of the tubular portion are properly aligned with the pressure sensing assembly of the spirometer. To insure such proper alignment, lines can be made on both the spirometer housing tube and the air tube at locations such that when the lines are mutually aligned the through ports of the tubular portion are properly aligned with the pressure-sensing assembly of the spirometer. The snugness of the fit between the air tube and the housing tube of the spirometer insures that the air tube can be used in conjunction with the spirometer without disturbing the through ports/pressure sensing assembly alignment. After use the air tube can be relatively easily removed from the spirometer housing tube and replaced by a new air tube.

The present air tubes can be designed and structured to be used with a retrofitted existing spirometer or with a spirometer specifically built for use with the air tubes.

It is particularly useful to have the tubular portion longer than the housing of the spirometer so that in use the tubular portion extends beyond both ends of the component of the housing of the spirometer to which the tubular portion is removably coupled. This feature is very attractive in preventing undue contamination of the spirometer housing by the user of the spirometer. Thus, the air which is exhaled by the patient passes through the tubular portion and does not come into significant or intimate contact with any portion of the housing of the spirometer.

In another broad aspect of the present invention, new spirometers are provided. The present spirometers comprise a housing; an air tube as described herein, a pressure sensing assembly positioned relative to the two through ports of the air tube to sense the pressure at each of the through ports; and an electronic assembly coupled to the pressure sensing assembly for generating signals, preferably electrical signals, indicative of the differential between the pressures sensed at each of the two through ports by the pressure sensing assembly. The electronic assembly can be disposed in the housing or can be located remote from the housing. For example, the housing can be a hand held component which is connected, for example, by wire or cable, to an electronic processing system which includes a substantial portion of the electronic assembly of the present spirometer. Alternately, the electronic assembly can be completely disposed in the spirometer housing so that a fully self-contained unit can be provided.

In a particularly useful embodiment, the present spirometers further comprise an additional electronic assembly coupled to the electronic assembly, optionally positioned outside of the housing, to process the signals from the electronic assembly and produce, and optionally display, performance signals indicative of the pulmonary performance of the patient using the spirometer.

Existing spirometers which can be retrofitted with the present air tubes often include a hand held unit including a breathing tube and a housing which is held by the patient using the spirometer. This housing preferably includes some electronics, for example, a differential pressure transducer, an amplifier and an analog-to-digital convertor. This hand held housing is coupled to a remote control station which typically contains relatively sophisticated electronics which control the operation of the spirometer, and analyze and interpret the pulmonary performance data collected by the spirometer.

In retrofitting applications, the existing hand held housing is replaced by a new hand held housing which is structured to employ air tubes in accordance with the present invention and to communicate with the existing remote control station. To achieve this communication, the new hand held housing preferably has one or more electronic components which correspond to each of the electronic components present in the replaced existing hand held housing. This retrofitting feature of the present invention is particularly attractive and advantageous because the hand held housing is inexpensive relative to the remote control station. Thus, the substantial advantages of using the present disposable/biodegradable air tubes can be obtained at reduced cost by owners/operators of existing spirometers. In effect, using the present retrofit system, the advantages of the present invention can be enjoyed without replacing the relatively expensive remote control station.

Although many of the features of the present invention are described separately, more than one or all of such features can be used in various combinations, provided that such features are not mutually inconsistent, and all of such combinations are within the scope of the present invention.

These and other aspects and advantages of the present invention are set forth in the following detailed description and claims, particularly when considered in conjunction with the accompanying drawings in which like parts bear like reference numerals.

BRIEF DESCRIPTION OF THE DRAWINGS

FIG. 1 is a somewhat schematic illustration showing a spirometer in accordance with the present invention.

FIG. 2 is a side view of a spirometer in accordance with the present invention showing a portion of the electronics disposed apart from the hand held unit.

FIG. 2A is a front side view of the spirometer shown in FIG. 2.

FIG. 3 is a partially cut away, top front view, in perspective, of the air tube used in the spirometer shown in FIG. 2.

FIG. 4 is a cross-sectional view taken generally along line 4—4 of FIG. 3.

FIG. 5 is a cross-sectional view taken generally along line 5—5 of FIG. 3.

FIG. 6 is a partially cut away, cross-sectional view taken generally along line 6—6 of FIG. 2.

FIG. 7 is a cross-sectional view taken generally along line 7—7 of FIG. 2.

FIG. 8 is a side view of an alternate embodiment of a spirometer in accordance with the present invention.

FIG. 9 is a back side view of the spirometer shown in FIG. 8.

DETAILED DESCRIPTION OF THE DRAWINGS

Referring to FIGS. 2 and 2A, a spirometer in accordance with the present invention, shown generally at 10, includes a disposable, biodegradable air tube 12, a housing 14 and control electronics 16. Spirometer 10 is what is commonly known as a differential pressure spirometer and, in general, operates in a manner similar to the spirometer disclosed in the above-noted Waterson et al U.S. Pat. No. 5,137,026.

Air tube 12 is described with reference to FIGS. 3, 4 and 5. Air tube 12 includes a first tubular segment 18, a second tubular segment 20 and a resistive element 22 located therebetween. Tubular segments 18 and 20 are made of biodegradable cardboard or heavy paper, for example, in a manner similar to how cardboard tubes are conventionally made, such as for use with bathroom tissue and the like products. The resistive element 22 is made of a biodegradable polymeric composition, such as compositions based on starch and unsaturated hydrocarbons or thermoplastic polymers or cellulose acetate. See, for example, U.S. Pat. Nos. 5,296,526; 5,292,782; and 5,288,318, the disclosures of each of which is incorporated in its entirety herein by reference. Resistive element 22 can be fabricated into the configuration described and shown herein using conventional plastics processing techniques, for example, injection molding.

First and second tubular segments 18 and 12 include through ports 24 and 26, respectively, which can be punched out or otherwise cut from the tubular segments before (or after) assembly of the air tube 12. These through ports 24 and 26 are positioned so that, in the assembled air tube 12, they lie on either side of, and are spaced apart equidistantly from, the resistive element 22. The centers of these ports 24 and 26 define a line which is parallel to the longitudinal axis 28 of air tube 12. Through ports 24 and 26 open directly into the hollow space 30 defined by the tubular segments 18 and 20.

Resistive element 22, which is preferably integrally formed, includes a flow restrictor 32 which extends into hollow space 30 around the circumference of the hollow space. Flow resistor 32 forms a passage which has a smaller cross-sectional area than does hollow space 30. Air passing from hollow space 30 across flow restrictor 32 causes a pressure differential which can be measured by sensing the pressure at through ports 24 and 26.

Resistive element 22 further includes a base 36 which is secure to and surrounds flow resistor 32. Base 36 includes a first shoulder surface 38 and a second shoulder surface 40 and an outwardly extending central portion 42. In addition, an outwardly extending button 44 is attached to one portion of the central portion 42. Button 44 is positioned to be diametrically opposed to the centers of first and second through ports 24 and 26.

Air tube 12 is assembled by bringing first tubular segment 18 and second tubular segment 20 in proximity to first shoulder surface 38 and second shoulder surface 40, respectively. Using a biodegradable adhesive, ultrasonic force and/or other bonding technique or techniques, the first and second tubular segments 18 and 20 are bonded to base means 36 substantially as shown in FIG. 4. After assembly, the air tube 12 is packaged and ready for shipment and use.

Air tube 12 includes an open inlet 46 and an open outlet 48. The area 50 surrounding the open inlet 46 is sized and adapted to be fitted into a human being's mouth. This mouthpiece area 50 is employed by the patient using spirometer 10 by placing the area into the mouth and exhaling into hollow space 30 of air tube 12.

When it is desired to use air tube 12, it is unpackaged and is coupled to housing 14. In particular, with reference to FIG. 2, housing tube 51 includes a L-shaped slot 52. Air tube is placed into housing tube 51 by placing button 44 into slot 52. The air tube is then moved into the housing tube 51 until the button 44 reaches the back wall 54 of slot 52. At this point, air tube 12 is rotated to fit the button 44 securely in the short portion 56 of slot 52. With the bottom 44 so positioned, air tube 12 is properly coupled to housing 14 so that first and second through ports 24 and 26 are in communication with the sensing ports of the pressure sensing legs, described hereinafter. At this point, spirometer 10 is ready for use. Note that air tube 12 is longer than housing tube 51 and, when properly coupled to the housing tube, extends beyond both ends of the housing tube. This feature is present in the other air tube/housing combinations specifically illustrated herein. The relatively long air tube reduces the risk of air exhaled from the spirometer user coming into effective contact with and contaminating the housing.

When it is desired to remove air tube 12 from housing tube 51, the air tube is rotated in a reverse direction and then pulled out of slot 52.

FIG. 1 illustrates the general operation of a spirometer, shown generally at 58, in accordance with the present invention. The air tube used in FIG. 1 is of a more simple design than air tube 12. This more simple air tube, shown generally at 60, is made of the same materials of construction as air tube 12. A single integral cardboard or heavy paper tube 62 is provided and defines a hollow through space 63, an open inlet 64, an open outlet 65, a mouthpiece area 66, and two through ports 67 and 68. Each of these components functions in substantially the same manner as does the corresponding component of air tube 12.

Resistive element 70 is simply an annular insert element of biodegradable polymeric material, as described elsewhere herein. This resistive element 70 is press-fit into the hollow space 63 of air tube 60. The housing tube 71 defines a hollow through space and includes an arrowhead 74 on its outside surface. The arrowhead 74 and index line 75 on the outside surface air tube 60 are positioned so that when the arrowhead and index line is aligned, as shown in FIG. 1, the through ports of air tube 60 communicate with the pressure sensing legs 76 and 78, respectively.

In addition, air tube 60 is sized to fit snugly in the through hole defined by the housing tube 71.

When it is desired to use spirometer 58, air tube 60 is placed in the through hole defined by housing tube 71. The air tube 60 is manipulated until the index line 75 and arrowhead 74 become aligned, again as shown in FIG. 1. At this point, air tube 112 is properly positioned and the spirometer 58 is ready for use.

The following is a general description of the operation of the remainder of the spirometer 58 after the air tube 60 is properly located and positioned relative to the pressure sensing legs 76 and 78. This general description is applicable using any spirometer, such as spirometer 10, in accordance with the present invention.

Through ports 67 and 68 communicate with pressure sensing legs 76 and 78, respectively. As a further protection against contamination, pressure sensing legs 76 and 78 may be equipped with filters, although this is not required. These pressure sensing legs 76 and 78 communicate with a differential pressure transducer 80, which may be, for example, a transducer sold by Motorola under the trademark MPX 2020D. The pressure transducer 80 generates an electrical signal on a pair of output wires 82 and 84, which signal is proportional to the differential pressure between pressure sensing legs 76 and 78. This signal is amplified by a differential amplifier stage 86 and fed into an analog-to-digital convertor 88 which converts the amplifier output into digital signals.

The output from convertor 88 is fed to a microprocessor 90, which is part of control electronics 16. The microprocessor 90 uses an algorithm stored in a ROM 92 to perform several calculations on the signal from convertor 88, and to display the results, e.g., volume and flow rate, on display 94, for example, a conventional monitor or liquid crystal display module. Microprocessor 90 is powered by a power source 91, for example, a connector capable of being coupled or connected to a source of conventional electric line voltage. Switch 96 can be activated to initiate the operation of the spirometer through microprocessor 90. The results during each measurement may be stored in a RAM 98 for future reference. An input/output port 100 may also be provided to allow for changing the programming of the microprocessor 90. Furthermore, the microprocessor 90 may be programmed so that on command it may download the results accumulated in RAM 98 through input/output port 100 to a printer or a computer.

Waterson et al U.S. Pat. No. 5,137,026 provides further details regarding the operation of such a spirometer.

In any event, when a patient has concluded one treatment or diagnostic exercise using the spirometer 10, the biodegradable air tube, for example, air tube 12 or air tube 60, is removed from the housing tube and is disposed of in an environmentally safe manner.

As shown in FIGS. 2 and 2A, the housing 14 is structured to be gripped in one hand of the user. For example, the shaft 102 of housing 14 is configured for easy hand gripping. In addition, finger indents 104 are provided to make hand holding this device even easier.

The embodiment shown in FIGS. 2 and 2A includes control electronics 16 located remote from hand held housing 14. Communication between convertor 88 and control electronics 16 occurs through cable 106 which can be connected to the convertor using jack 105, such as a conventional RJ-11 quick connect jack, on housing 14. Convertor 88, amplifier stage 86 and pressure transducer 80 can be powered through cable 106 from microprocessor 90 and power source 91. Alternatively, the electronics in the housing 14 can be independently powered by a battery pack, such as a conventional rechargeable nickel-cadmium battery. If such a battery pack is used the housing 14 includes a port through which the battery pack can be charged.

In the embodiment shown in FIGS. 2 and 2A, microprocessor 90 can be a dedicated microprocessor including a simple keyboard structured and adapted specifically to control the operation of a spirometer. Alternatively, the microprocessor 90 may be a component of a general purpose, personal computer including a full-sized keyboard, video monitor, hard disk drive and printer. The dedicated microprocessor is particularly advantageous because of its relative simplicity, reduced cost and ease of use.

In addition, the shaft 102 of housing 14 includes a tapered portion 107, as shown in FIG. 2A, which facilitates placing and maintaining the housing on a flat surface, for example, between uses.

The embodiment shown in FIGS. 2 and 2A is useful as a completely new spirometer or the air tube 12 and housing 14 can be used to retrofit an existing spirometer. For example, an existing spirometer includes a hand held unit including a permanent breathing tube, pressure sensing legs, a pressure transducer, an amplifier and an analog-to-digital convertor, and is connected to a dedicated control system, which functions in a manner substantially similar to control electronics 16. Simply by replacing the existing hand held unit with housing 14 and the components coupled to or disposed in the housing, a retrofitted spirometer is produced which has many of the advantages of the present invention.

A still further embodiment of the present invention is illustrated in FIGS. 8 and 9. This spirometer, shown generally at 210, is, except as expressly stated herein, structured in a manner similar to spirometer 10. Components of spirometer 210 which correspond to components of spirometer 10 have corresponding reference numerals increased by 200.

The primary differences between spirometer 210 and spirometer 10 have to do with the configuration of air tube 212, the configuration of the housing tube 251 and the location of the electronics.

Air tube 212 is structured substantially similar to air tube 60 except that in the region near open outlet 248, two positioning ports 107 and 108 are provided.

Housing tube 251 is structured to act as a cradle for air tube 212 rather than surrounding the air tube, as do housing tubes 51 and 71. In addition, housing tube 251 includes two upwardly extending projections 109 and 110 which are positioned to be received by positioning ports 107 and 108, respectively, when air tube 212 is coupled to housing tube 251. With projections 109 and 110 mated to or received by positioning ports 107 and 108, the ports 224 and 226 are properly aligned with the pressure sensing legs 76 and 78.

An additional feature of spirometer 210 is that all of the electronic circuitry, shown generally at 111, that is pressure transducer 80, amplifier stage 86, converter 88 and control electronics 16, is located in housing 214. Thus, as shown in FIGS. 8 and 9, control keyboard 112 of microprocessor 90 is located on the shaft 302 of housing 214. In addition, the display 94 is located on the housing 214. In spirometer 210, the power source 91 is a battery pack, such as a conventional rechargeable nickel-cadmium battery, and is located within housing 214. Port 114 on housing 214 is adapted to provide communication between battery pack 91 and a conventional battery charger to recharge the battery pack when needed. I/O port 100 is also carried by housing 214 and provides convenient communication between microprocessor 90 and a computer or printer, when it is desired to download information from electronic circuitry 111 to such other device. Spirometer 210 is a self-contained unit that can be operated by a single patient.

In order to operate spirometer 210, air tube 212 is coupled to housing tube 251 so that projections 109 and 110 mate with positioning ports 107 and 108, respectively. The patient then turns on switch 96 and uses spirometer 210 for any treatment and/or diagnostic procedure desired. When it is desired to remove air tube 212 from housing tube 251, the biodegradable air tube 212 is simply picked up from the housing tube 212 and can be discarded in an environmentally acceptable manner.

One important feature of the present invention is that the air tubes are at least partially, preferably completely, biodegradable. This feature allows for rapid and frequent removal and replacement of air tubes in an economically and environmentally effective manner so that the risks of contamination are reduced relative to a spirometer having a permanent air tube. In addition, the biodegradable air tubes, in accordance with the present invention, are easily and inexpensively made, promote operator compliance in disposing of the air tube after each patient/treatment, and can be disposed of in an environmentally acceptable manner, thus reducing the burden on the environment caused by frequent changing or replacement of the air tubes.

While this invention has been described with respect to various specific examples and embodiments, it is to be understood that the invention is not limited thereto and that it can be variously practiced with the scope of the following claims.

What is claimed is:

1. An air tube for use in a differential pressure spirometer comprising:

a tubular portion defining an open inlet, an open outlet and a hollow space therebetween, and being sized and adapted to be removably coupled to a housing of a differential pressure spirometer;

a resistive element located in said hollow space and being sized and adapted to cause a pressure difference as air flows in said hollow space across said resistive element; and at least one through port located in said tubular portion which opens directly to said hollow space and is spaced apart from said resistive element, provided that said air tube is disposable and at least a major portion of said tubular portion is biodegradable.

2. The air tube of claim 1 wherein said tubular portion includes an area adapted to come into direct contact with the mouth of a human being during use of said air tube.

3. The air tube of claim 1 wherein said tubular portion is made of a material selected from the group consisting of cardboard, paper, biodegradable polymers and mixtures thereof.

4. The air tube of claim 1 wherein said tubular portion is made of cardboard.

5. The air tube of claim 1 wherein all of said tubular portion is biodegradable.

6. The air tube of claim 1 which includes two through ports located in said tubular portion each of which opens directly to said hollow space and is spaced apart from said resistive element which is located therebetween.

7. The air tube of claim 6 wherein each of said two through ports is equidistant from said resistive element.

8. The air tube of claim 1 wherein said resistive element is made of a polymeric material.

9. The air tube of claim 1 wherein said resistive element is positioned in said hollow space and partially occludes said hollow space.

10. The air tube of claim 1 which is substantially totally biodegradable.

11. The air tube of claim 1 which further comprises a positioning means adapted to cooperate with the housing of the spirometer to properly position said air tube relative to the housing of the spirometer.

12. A combination comprising:

a housing;

an air tube of claim 1 removably coupled to said housing;

a pressure sensing assembly positioned relative to said through port to sense the pressure in said through port; and an electronic assembly disposed in said housing and coupled to said pressure sensing assembly for generating signals based on the pressure sensed in said through port by said pressure sensing assembly.

13. The combination of claim 12 wherein said housing is sized and adapted to be held in a hand of a patient using said air tube, and which further comprises an additional electronic assembly coupled to said electronic assembly and positioned outside of said housing to process said signals to produce and display performance signals indicative of the pulmonary performance of the patient using said air tube.

14. The combination of claim 12 wherein said housing is sized and adapted to be held in a hand of a patient using said air tube, and which further comprises an additional electronic assembly coupled to said electronic assembly and disposed in said housing to process said signals to produce and display performance signals indicative of the pulmonary performance of the patient using said air tube.

15. The combination of claim 14 which further comprises a rechargeable battery disposed in said housing to power said electronic assembly and said additional electronic assembly.

16. The combination of claim 12 wherein said housing includes a housing component to which said tubular portion is removably coupled, all of said tubular portion is biodegradable, and said tubular portion is longer than said housing component and extends beyond both ends of said housing component.

17. An air tube for use in a differential pressure spirometer including a housing comprising:

a tubular portion made of a material selected from the group consisting of cardboard, paper, biodegradable polymers and mixtures thereof, defining an open inlet, an opposing open outlet and a hollow space therebetween, and being sized and adapted to be removably coupled to the housing of the differential pressure spirometer, said tubular portion including a positioning assembly sized and adapted to cooperate with the housing of the differential pressure spirometer to properly position said tubular portion relative to the housing;

a resistive element located in said hollow space and sized and adapted to cause a pressure difference as air flows in said hollow space across said resistive element; and a through port located in said tubular portion which opens directly to said hollow space, and is spaced apart from said resistive element.

18. The air tube of claim 17 which includes a second through port located in said tubular portion which opens directly to said hollow space and is spaced apart from said resistive element which is located between said through port and said second through port.

19. An air tube for use in a differential pressure spirometer comprising:

a tubular portion defining an open inlet, an open outlet and a hollow space therebetween, and being sized and adapted to be removably coupled to a housing of a differential pressure spirometer;

a resistive element located in said hollow space and being sized and adapted to cause a pressure difference as air flows in said hollow space across said resistive element; and at least one through port located in said tubular portion which opens directly to said hollow space and is spaced apart from said resistive element, provided that said air tube is disposable and all of said tubular portion is made of a material selected from the group consisting of cardboard, paper and mixtures thereof.

* * * * *